(12) United States Patent
Kawaguchi

(10) Patent No.: US 9,895,513 B2
(45) Date of Patent: Feb. 20, 2018

(54) CATHETER

(71) Applicant: TERUMO KABUSHIKI KAISHA, Shibuya-ku, Tokyo (JP)

(72) Inventor: Michihiro Kawaguchi, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 4 days.

(21) Appl. No.: 14/724,948

(22) Filed: May 29, 2015

(65) Prior Publication Data

US 2015/0265806 A1    Sep. 24, 2015

Related U.S. Application Data

(63) Continuation of application No. PCT/JP2013/081952, filed on Nov. 27, 2013.

(30) Foreign Application Priority Data

Nov. 30, 2012    (JP) .................. 2012-262764

(51) Int. Cl.
*A61M 25/00*    (2006.01)
*A61M 25/09*    (2006.01)

(52) U.S. Cl.
CPC .... *A61M 25/0097* (2013.01); *A61M 25/0028* (2013.01); *A61M 25/09* (2013.01); *A61M 25/09041* (2013.01)

(58) Field of Classification Search
CPC .......... A61M 25/0097; A61M 25/0028; A61M 25/09; A61M 25/09041; A61M 25/0014
See application file for complete search history.

(56) References Cited

U.S. PATENT DOCUMENTS 4,444,203 A * 4/1984 Engelman ......... A61M 25/0693
                                                    600/576
4,781,703 A * 11/1988 Walker .............. A61M 25/0014
                                                    604/264

(Continued)

FOREIGN PATENT DOCUMENTS

EP    0 109 657 A1    5/1984
JP    59-103674 A     6/1984

(Continued)

OTHER PUBLICATIONS

Partial Supplementary European Search Report dated Jun. 27, 2016 by the European Patent Office in corresponding European Patent Application No. 13858046.9.

(Continued)

*Primary Examiner* — Lauren M Peng
(74) *Attorney, Agent, or Firm* — Buchanan Ingersoll & Rooney P.C.

(57) ABSTRACT

A hub of a catheter has a first tapered portion in which an inner diameter is reduced toward a distal direction from a proximal opening portion, a second tapered portion in which an inner diameter is reduced at a ratio greater than that of the first tapered portion from a distal end of the first tapered portion toward the distal direction, and a third tapered portion in which an inner diameter is reduced at a ratio smaller than that of the second tapered portion from a distal end of the second tapered portion toward the distal direction.

20 Claims, 5 Drawing Sheets

(56) References Cited

U.S. PATENT DOCUMENTS

| | | | | |
|---|---|---|---|---|
| 5,156,792 | A | * | 10/1992 | Holdaway ......... A61M 25/0606 264/230 |
| 5,830,189 | A | | 11/1998 | Chang |
| 6,355,027 | B1 | | 3/2002 | Le et al. |
| 9,302,077 | B2 | * | 4/2016 | Domonkos ......... A61M 5/3273 |
| 2003/0220628 | A1 | * | 11/2003 | Klisch ............... A61M 25/0097 604/524 |
| 2004/0267213 | A1 | * | 12/2004 | Knapp ................. A61B 1/307 604/284 |
| 2006/0178635 | A1 | | 8/2006 | Callaway |
| 2012/0022470 | A1 | | 1/2012 | Kuniyasu et al. |

FOREIGN PATENT DOCUMENTS

| | | |
|---|---|---|
| JP | 9-637 A | 1/1997 |
| JP | 10-216240 A | 8/1998 |
| JP | 2010-178807 | 8/2010 |
| WO | 2007/132444 A2 | 11/2007 |

OTHER PUBLICATIONS

English translation of Notification of Reasons for Refusal dated Sep. 28, 2017 in corresponding Japanese Patent Application No. 2014-549872.

* cited by examiner

CATHETER

CROSS-REFERENCES TO RELATED APPLICATIONS

This application is a continuation of International Application No. PCT/JP2013/081952 filed on Nov. 27, 2013, and claims priority to Japanese Application No. 2012-262764 filed on Nov. 30, 2012, the entire content of both of which is incorporated herein by reference.

TECHNICAL FIELD

The present disclosure generally relates to a catheter.

BACKGROUND DISCUSSION

Conventionally, inspecting and treating a lesion area (for example, constricted area) within a biological organ by introducing a catheter into the biological organ such as a blood vessel or the like has been widely performed. In general, this kind of catheter has an elongated shaft constituting a catheter main body and a hub which is connected to a proximal portion of the shaft (for example, refer to U.S. Pat. No. 6,355,027 and JP-A-9-637).

In use of such a catheter, it may be necessary to selectively advance the shaft into blood vessels which are complicatedly branched in a living body or lumens in a living body in order to make a distal end of the catheter reach a target area in a living body. For this reason, in general, a guide wire is inserted through a lumen of a catheter, which is then run through a blood vessel or a lumen in a living body along the guide wire in a state where a distal end of the guide wire is made to precede the distal end of the catheter.

However, in some cases, the guide wire is used by bending (angling) one or more portions, for example, a plurality of a distal portion of the guide wire in advance in order to select a blood vessel or control the direction of the distal end of the catheter. When inserting the guide wire of which a distal portion is angled in this manner into the catheter from a proximal opening portion of a hub of the catheter, the most distal portion of the guide wire can come into contact with a part of an inner peripheral surface of the hub and the guide wire can advance to the hub while the other end of the guide wire can come into contact with an inner peripheral surface of the hub on a side opposite to the contact area. In this case, a luer taper in which the inner diameter is reduced at a constant ratio toward a distal direction can be provided in the conventional hub. Therefore, the inner diameter of the hub becomes smaller toward a distal side and the frictional resistance between the guide wire and the inner peripheral surface of the hub becomes greater along with the reduction of the inner diameter. For this reason, the movement of the guide wire can be inhibited on the inner peripheral surface of the hub, and therefore, in some cases, it can be difficult to further move the guide wire to the distal side.

SUMMARY

In accordance with an exemplary embodiment, the present disclosure has been made in consideration of such a problem, and the present disclosure generally relates to a catheter in which a distal end of a guide wire, which is bent, can be smoothly inserted into a lumen of a shaft of the catheter by reducing the movement resistance of the distal end of the guide wire against a hub when inserting the guide wire into the catheter from a proximal opening portion of the hub of the catheter.

In accordance with an exemplary embodiment, a catheter is disclosed, which can include a shaft constituting a catheter main body, and a hub which is provided at a proximal end of the shaft and has a hub lumen that communicates with a lumen of the shaft, and a proximal opening portion. The hub has a first tapered portion in which the inner diameter is reduced toward a distal direction from the proximal opening portion, a second tapered portion in which the inner diameter is reduced at a ratio greater than that of the first tapered portion from a distal end of the first tapered portion toward the distal direction, and a third tapered portion in which the inner diameter is reduced at a ratio smaller than that of the second tapered portion from a distal end of the second tapered portion toward the distal direction.

In accordance with an exemplary embodiment, according to the aforesaid configuration, when inserting a guide wire, of which a distal portion is bent, from a proximal side of the hub, the distal portion of the guide wire is guided to a direction of returning the shape of the guide wire to a linear shape, by the second tapered portion in which the inclination angle is larger than that of the first tapered portion. Accordingly, the inclination of the distal portion of the guide wire with respect to an axis of the hub can be reduced at a comparatively early stage (on an operator side within a hub lumen), which can result in a decrease in frictional resistance between an inner peripheral surface of the hub and the distal portion of the guide wire, and therefore, the distal portion of the guide wire can move relatively easily in the distal direction. Accordingly, the guide wire can be smoothly inserted into the shaft without inhibition of the movement of the guide wire due to the inner peripheral surface of the hub.

In accordance with an exemplary embodiment, the hub may have a straight portion in which the inner diameter is constant from a distal end of the third tapered portion toward the distal direction. According to this configuration, the guide wire can be smoothly inserted into the shaft as described above.

In accordance with an exemplary embodiment, the hub may be formed of a material having transparency, and a plurality of channels extending in an axial direction may be provided in a portion of the hub which corresponds to the second tapered portion. According to this configuration, with the provision of the channels, it can be relatively easy to visually recognize whether there is an end portion of the guide wire in the second tapered portion.

In accordance with an exemplary embodiment, the inner shape of the second tapered portion on a longitudinal cross section of the hub may have a portion which is curved so as to be raised toward the inside of the hub. According to this configuration, the frictional resistance can be reduced by reducing the contact area between the distal portion of the guide wire and the second tapered portion, and therefore, the guide wire can relatively easily pass through the second tapered portion.

In accordance with an exemplary embodiment, the smoothness on an inner peripheral surface may vary among the first tapered portion, the second tapered portion, and the third tapered portion. According to this configuration, the frictional resistance between the distal portion of the guide wire and the second tapered portion can be further reduced when guiding the guide wire using the second tapered portion and to smoothly perform an insertion operation of the guide wire, by, for example, increasing the smoothness of the second tapered portion more than those of the first and third tapered portions.

In accordance with an exemplary embodiment, a stepped portion coming into contact with a proximal portion of the shaft may be provided in the hub, and the material constituting the shaft may cover the stepped portion and be provided further on a proximal side than the stepped portion. According to this configuration, when inserting the guide wire from a distal end of the catheter and passing a proximal end of the guide wire through the hub, the proximal end of the guide wire can be favorably guided by the material of the shaft covering the stepped portion of the hub. Accordingly, the proximal end of the guide wire can smoothly move in the proximal direction within the hub.

In accordance with an exemplary embodiment, according to the catheter of the present disclosure, the distal end of the guide wire can be smoothly inserted into the lumen of the shaft of the catheter.

In accordance with an exemplary embodiment, a catheter is disclosed comprising: a shaft; and a hub at a proximal end of the shaft, the hub having a hub lumen that communicates with a lumen of the shaft and a proximal opening portion, and wherein the hub has a first tapered portion in which an inner diameter is reduced toward a distal direction from the proximal opening portion, a second tapered portion in which an inner diameter is reduced at a ratio greater than that of the first tapered portion from a distal end of the first tapered portion toward the distal direction, and a third tapered portion in which an inner diameter is reduced at a ratio smaller than that of the second tapered portion from a distal end of the second tapered portion toward the distal direction

DETAILED DESCRIPTION

Hereinafter, a catheter according to the present disclosure will be described with reference to the accompanying drawings using an exemplary embodiment.

Figure 1:
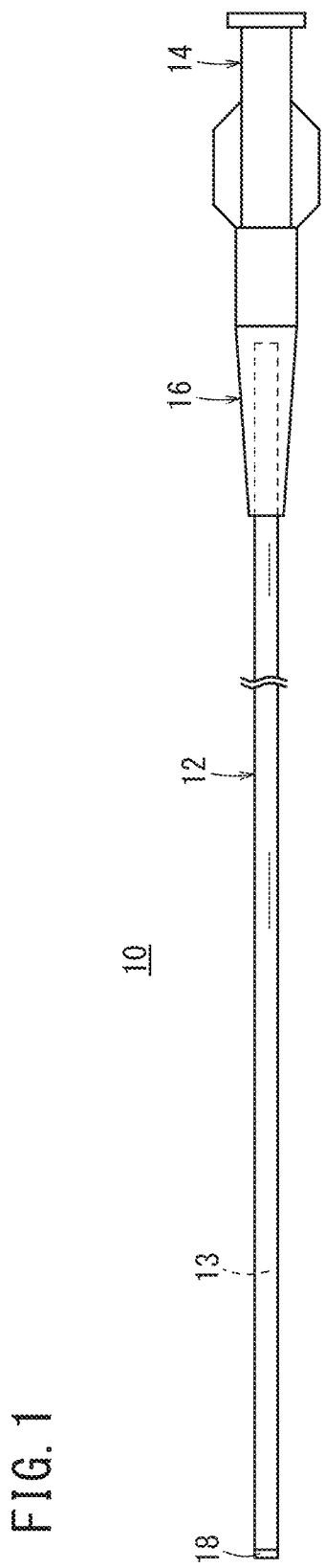
FIG. 1 is a partially omitted side surface view of a catheter according to one embodiment of the present invention.

FIG. 1 is a partially omitted side surface view of a catheter 10 according to an embodiment of the present disclosure. The catheter 10 can be used for, for example, injecting a drug for treatment or injecting a contrast agent for diagnosis by being inserted into a blood vessel or a lumen in a living body and making a distal portion of the catheter reach a target area. As shown in FIG. 1, the catheter 10 includes an elongated shaft 12 with a thin diameter, a hub 14, which is connected to a proximal end of the shaft 12, and a strain relief 16, which is provided in a connection portion to the hub 14 of the shaft 12.

The shaft 12 constitutes a main body of the catheter which is inserted into body lumens such as blood vessels, and is an elongated tubular member with a thin diameter in which a lumen 13 (also refer to FIG. 2) communicating between the distal end and the proximal end is formed and which has flexibility. The length of the shaft 12 can be, for example, about 500 mm to 2000 mm and, for example, preferably about 1000 mm to 1500 mm.

The outer diameter of the shaft 12 can be, for example, about 0.3 mm to 3 mm and, for example, preferably 0.4 mm to 2 mm. The inner diameter of the shaft 12 can be, for example, about 0.2 mm to 2.5 mm and, for example, preferably about 0.3 mm to 1.8 mm. The outer diameter and the inner diameter of the shaft 12 may become smaller toward the distal side. The most distal portion of the shaft 12 may have a taper.

A radiopaque marker (contrast marker) 18 can be fixed onto an outer peripheral surface in the vicinity of the most distal portion of the shaft 12. The radiopaque marker 18 can be formed of a material, such as gold, platinum, or the like, which has radiopacity so as to visually check the position of the distal end of the catheter 10 in a living body under X-ray imaging.

The hub 14 is a member with a hollow structure which holds the proximal end of the shaft 12 at the distal end of the hub, and can be formed such that other instruments such as a syringe or the like can be connected to the proximal end of the hub. The hub 14 can be formed of, for example, a hard resin or the like such as polycarbonate, polyethylene, polypropylene, and the like. In the present embodiment, the hub 14 is formed of a material (such as polycarbonate or the like) which has transparency. Accordingly, it is possible to check whether there is an end portion of the guide wire 42 (refer to FIG. 3A or the like) or the like in the hub 14 when inserting the guide wire 42 or the like therethrough, which can be preferable.

The strain relief 16 can be used for preventing the shaft 12 from being bent (kinked) at the connection portion to the hub 14 and can be a resin member which is formed in, for example, a tapering tubular shape and has adequate flexibility and rigidity. The strain relief 16 can be formed of the same material as the constituent material of the shaft 12.

Figure 2:
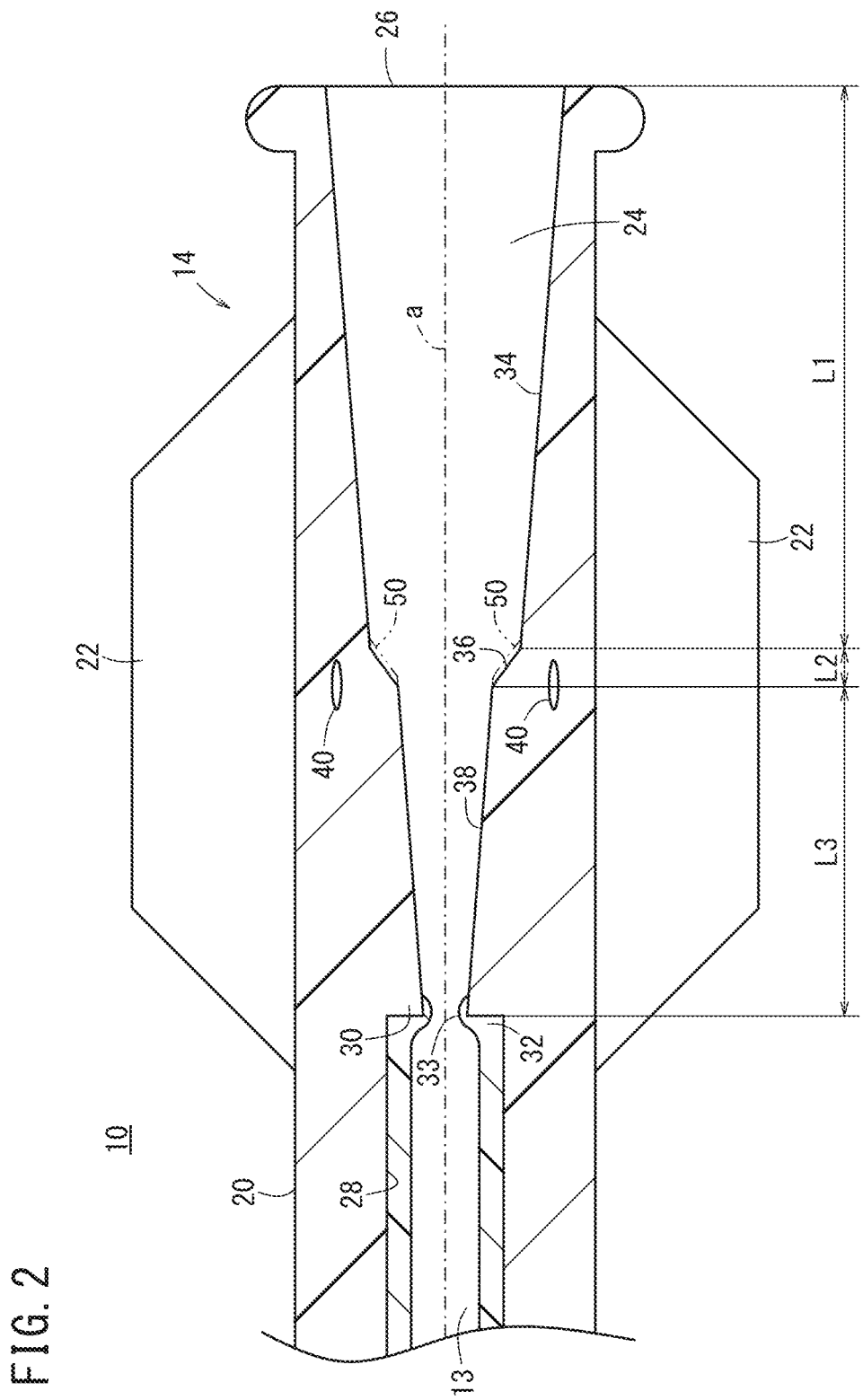
FIG. 2 is a partially omitted longitudinal cross-sectional view of a hub of the catheter shown in FIG. 1.

Next, a specific configuration of the hub 14 will be described. FIG. 2 is a partially omitted longitudinal cross-sectional view of the hub 14. As shown in FIG. 2, the hub 14 is configured to have a hollow body portion 20 and a plurality of (two in the example shown in the drawing) blade portions 22 which protrude from an external surface of the body portion 20. The body portion 20 has a hub lumen 24, which communicates with the lumen 13 of the shaft 12, and a proximal opening portion 26. In addition, in the hub 14, a shaft holding unit 28 can be provided further on the distal side than the hub lumen 24. A proximal portion 32 of the shaft 12 is held by and fixed to the shaft holding unit 28. A stepped portion 30 in which the diameter is reduced with respect to a distal end of the hub lumen 24 is provided on a proximal side of the shaft holding unit 28, and the proximal portion 32 of the shaft 12 comes into contact with the stepped portion 30.

In the present embodiment, the hub 14 is provided at a rear end of the shaft 12 through insert molding, and a part of the material (resin material) constituting the shaft 12 protrudes to the side of the hub lumen 24. In accordance with an exemplary embodiment, for example, the material constituting the shaft 12 covers the stepped portion 30 and is provided further on the proximal side than the stepped portion 30. For this reason, as shown in FIG. 2, the inner peripheral portion of the proximal portion 32 of the shaft 12 has a portion 33 in which the diameter is reduced toward a proximal direction in a portion of the stepped portion 30.

In accordance with an exemplary embodiment, the shaft 12 is not limited to being formed through the insert molding with respect to the hub 14. For example, the hub 14 and the shaft 12 may be separately produced and bonded together through appropriate bonding means such as adhesion, heat fusion or the like by inserting the proximal portion 32 of the shaft 12 into a distal end of the hub 14.

As shown in FIG. 2, the hub 14 has a first tapered portion 34 in which the inner diameter is reduced toward a distal direction from the proximal opening portion 26; a second tapered portion 36 in which the inner diameter is reduced at a ratio greater than that of the first tapered portion 34 from a distal end of the first tapered portion 34 toward the distal direction; and a third tapered portion 38 in which the inner diameter is reduced at a ratio smaller than that of the second tapered portion 36 from a distal end of the second tapered portion 36 toward the distal direction. The hub lumen 24 is constituted by the first tapered portion 34, the second tapered portion 36, and the third tapered portion 38.

In accordance with an exemplary embodiment, the first tapered portion 34, the second tapered portion 36, and the third tapered portion 38 are provided in the hub 14 from the proximal side to the distal side. In accordance with an exemplary embodiment, the inclination angle of the second tapered portion 36 with respect to an axis a of the hub 14 is greater than that of the first tapered portion 34 with respect to the axis a and the inclination angle of the third tapered portion 38 with respect to the axis a of the hub 14 is smaller than that of the second tapered portion 36 with respect to the axis a.

The first tapered portion 34 is constituted as a luer taper to which other instruments (for example, a syringe or the like) can be connected. When inserting a guide wire 42 (refer to FIG. 3A or the like), of which a distal portion 43 is bent, from the proximal side of the hub 14, the first tapered portion 34 guides the distal portion 43 of the guide wire 42 to a central side of the hub 14 by an inner peripheral surface in which the diameter is reduced toward the distal direction. The length L1 along the axis a of the first tapered portion 34 can be, for example, about 10 mm to 40 mm and, for example, preferably about 20 mm to 35 mm.

In accordance with an exemplary embodiment, the second tapered portion 36 is a portion of which the inclination is greater than that of the first tapered portion 34 and has a function of guiding the distal portion 43 of the guide wire 42 to a direction of returning the shape of the guide wire 42 to a linear shape when inserting the guide wire 42, of which the distal portion 43 is bent, from the proximal side of the hub 14. Note that the details of the function will be described later. The length L2 along the direction of the axis a of the second tapered portion 36 can be, for example, about 0.5 mm to 2 mm and, for example, preferably about 1 mm to 2 mm. The length L2 may be set to be shorter than the length L1. Accordingly, the bending angle of the distal portion 43 of the guide wire 42 can be reduced over a short distance. The inclination angle with respect to the axis a of the second tapered portion 36 can be, for example, about 5 degrees to 45 degrees and, for example, preferably about 10 degrees to 20 degrees.

In accordance with an exemplary embodiment, the third tapered portion 38 is a portion of which the inclination is smaller than that of the second tapered portion 36 and which receives the distal portion 43 of the guide wire 42 which has passed through the second tapered portion 36 when inserting the guide wire 42, of which the distal portion 43 is bent, from the proximal side of the hub 14 to guide the distal portion of the guide wire to the lumen 13 of the shaft 12 which is provided on the distal side of the third tapered portion while guiding the distal portion 43 to the direction of further returning the shape of the guide wire to a linear shape. The length L3 along the direction of the axis a of the third tapered portion 38 can be, for example, about 2 mm to 15 mm and, for example, preferably about 5 mm to 10 mm.

The inclination angle with respect to the axis a of the third tapered portion 38 can be, for example, greater than 0 degrees and, for example, smaller than or equal to 15 degrees and, for example, preferably about 1 degree to 5 degrees. The inclination angle with respect to the axis a of the third tapered portion 38 may be the same as or different from that of the first tapered portion 34 with respect to the axis a.

The smoothness on the inner peripheral surface may vary among the first tapered portion 34, the second tapered portion 36, and the third tapered portion 38. Accordingly, the sliding resistance between the most distal portion 44 (refer to FIG. 3A or the like) of the guide wire 42 and the second tapered portion 36 may be reduced by, for example, increasing the smoothness of the second tapered portion 36 more than those of the first and third tapered portions 34 and 38.

As shown in FIG. 2, a plurality of channels 40 extending in the axial direction (axis a direction) may be provided in a portion (in a wall portion) of the hub 14, which corresponds to the second tapered portion 36. The plurality of channels 40 can be, for example, ventilation holes, which exist in the resin material constituting the hub 14, and are disposed at intervals in a circumferential direction around the axis a. In the present embodiment, the hub 14 is formed of a material having transparency, and therefore, the plurality of channels 40 can be visually recognized from the outside of the hub 14.

Figure 3A:
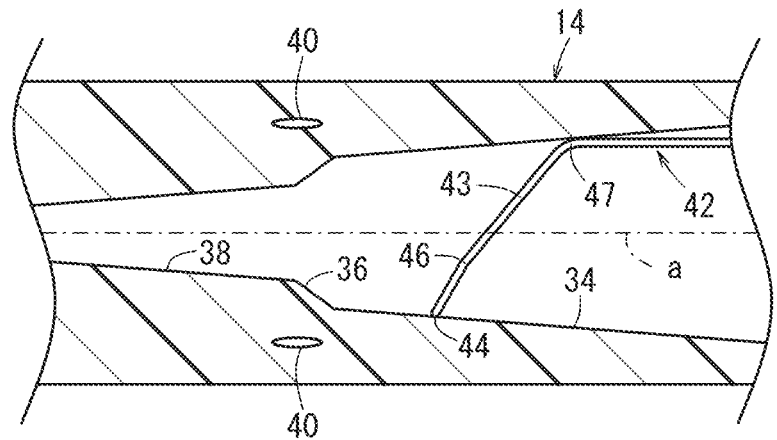
FIG. 3A is a first view for describing an operation of inserting a guide wire from a proximal side of the hub.
Figure 3B:
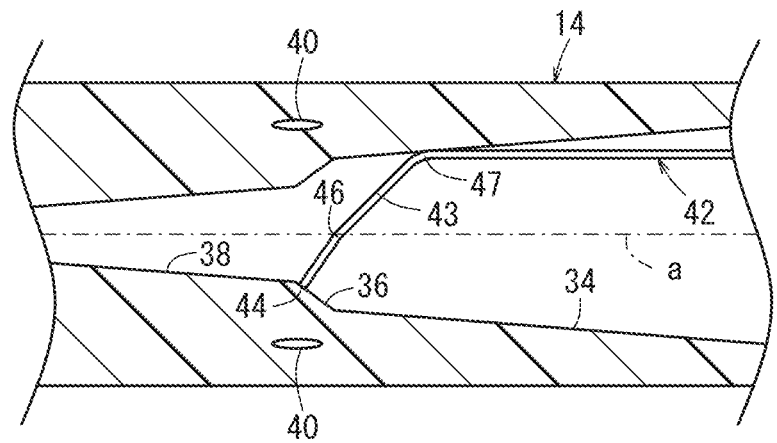
FIG. 3B is a second view for describing an operation of inserting the guide wire from the proximal side of the hub.
Figure 3C:
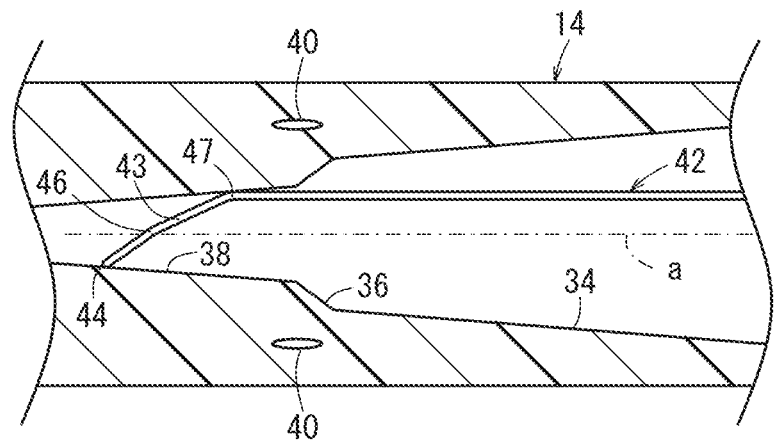
FIG. 3C is a third view for describing an operation of inserting the guide wire from the proximal side of the hub.

The catheter 10 according to the present embodiment is basically constituted as described above. Hereinafter, the action and the effect of the catheter 10 will be described with reference to FIGS. 3A to 3C. In this example, an operation of inserting the guide wire 42, of which the distal portion 43 is bent, from the proximal side (proximal opening portion 26) of the hub 14 will be described. In FIGS. 3A to 3C, the distal portion 43 of the guide wire 42 is bent so as to have two bent sections 46 and 47. However, the present disclosure can be applied to a case where there is only one bent section. The most distal portion 44 of the guide wire 42 is formed to be round.

As shown in FIG. 3A, when the guide wire 42, of which the distal portion 43 is bent, starts to be inserted from the proximal side of the hub 14, first, the most distal portion 44 of the guide wire 42 abuts on a part of an inner peripheral surface of the first tapered portion 34 and the other section (bent section 47 in FIG. 3A) of the guide wire 42 abuts on the other part (portion located on a side opposite to the portion in which the most distal portion 44 comes into contact with, and further on the proximal side than the portion) of the inner peripheral surface of the first tapered portion 34.

When the guide wire 42 is further pushed to the hub 14 in the distal direction, the guide wire 42 moves in the distal direction while the most distal portion 44 and the bent section 47 slide on the inner peripheral surface of the hub 14. As shown in FIG. 3B, when the most distal portion 44 of the guide wire 42 reaches the second tapered portion 36, the bent distal portion 43 of the guide wire 42 is guided in a direction of returning the shape of the guide wire to a linear shape, by the most distal portion 44 of the guide wire 42 being pushed to the axis a side of the hub 14 due to the second tapered portion 36. For example, the bending angle of the distal portion 43 of the guide wire 42 can be reduced by the action of the second tapered portion 36 along with the movement of the guide wire 42 in the distal direction.

As shown in FIG. 3C, when the most distal portion 44 of the guide wire 42 reaches the third tapered portion 38 exceeding the second tapered portion 36 (boundary between the second tapered portion 36 and the third tapered portion 38) by further advancing the guide wire 42 in the distal direction, the bending angle of the distal portion 43 of the guide wire 42 is further reduced due to the third tapered portion 38. In this case, the distal portion 43 of the guide wire 42 is already in a state where the bending angle is small when passing through the second tapered portion 36, and therefore, the frictional resistance (sliding resistance) between the most distal portion 44 and the inner peripheral surface of the hub 14 due to a restoring force of the bent section 47 of the guide wire 42 to its original state is small. In addition, when the bent section 47 of the guide wire 42 reaches the third tapered portion 38 exceeding the second tapered portion 36 (boundary between the second tapered portion 36 and the third tapered portion 38) by further advancing the guide wire 42 in the distal direction, the bending angle of the distal portion 43 of the guide wire 42 can be further reduced. For this reason, the frictional resistance (sliding resistance) between the most distal portion 44 and the inner peripheral surface of the hub 14 is further reduced. In this manner, when the frictional resistance between the most distal portion 44 and the inner peripheral surface of the hub 14 is small, even in a state where the distal portion 43 of the guide wire 42 is inserted up to the distal side of the hub 14, the pushing force of the guide wire 42 from the operator side can be efficiently transmitted up to the distal portion 43 of the guide wire 42, and therefore, the distal portion 43 of the guide wire 42 can move relatively easily in the distal direction.

As described above, according to the catheter 10 relating to the present embodiment, when inserting the guide wire 42, of which the distal portion is angled, from the proximal side of the hub 14, the distal portion 43 of the guide wire 42 is guided in a direction of returning the shape of the guide wire 42 to a linear shape, by the second tapered portion 36 in which the inclination angle is larger than that of the first tapered portion 34. Accordingly, the inclination of the distal portion 43 of the guide wire 42 with respect to the axis a of the hub 14 can be reduced at a comparatively early stage (on a base side within the hub lumen 24), which results in a decrease in the frictional resistance between the inner peripheral surface of the hub 14 and the most distal portion 44 of the guide wire 42, and therefore, the most distal portion 44 of the guide wire 42 can move relatively easily in the distal direction. Accordingly, the guide wire 42 can be smoothly inserted into the lumen 13 of the shaft 12 without inhibition of the movement of the guide wire 42 due to the inner peripheral surface of the hub 14.

In addition, in the case of the present embodiment, the hub 14 can be formed of a material having transparency, and the plurality of channels 40 extending in the axis a direction are provided in a portion of the hub 14 which corresponds to the second tapered portion 36. According to this configuration, with the provision of the channels 40, it can be relatively easy to visually recognize whether there is the distal portion 43 of the guide wire 42 in the second tapered portion 36. For example, when an end portion (distal portion 43 or proximal portion) of the guide wire 42 is positioned in the second tapered portion 36, the presence of the end portion of the guide wire 42 can be easily checked through the refraction action of light in the plurality of channels 40 which are provided in portions of the second tapered portion 36.

In accordance with an exemplary embodiment, a plurality of minute protrusions 50 which extend in a longitudinal direction (axial direction) in an inner peripheral portion of the second tapered portion 36 may be provided at intervals in the circumferential direction as shown in FIG. 2 in addition to or instead of the plurality of channels 40. In addition, the plurality of minute protrusions 50 extending in the longitudinal direction (axial direction) may be adjacently provided at slight intervals in the circumferential direction (through a groove between protrusions 50). With the provision of such protrusions 50, the distal portion 43 can be smoothly guided in the distal direction while inhibiting shaking in the circumferential direction due to the movement of the distal portion 43 of the guide wire 42 along the protrusions 50 when the distal portion 43 is guided by the second tapered portion 36.

As described above, the smoothness on the inner peripheral surface may vary among the first tapered portion 34, the second tapered portion 36, and the third tapered portion 38. For example, by increasing the smoothness of the second tapered portion 36 more than the first and third tapered portions 34, 38, the frictional resistance between the distal portion 43 of the guide wire 42 and the second tapered portion 36 can be reduced and an insertion operation of the guide wire 42 can be performed smoothly, when guide wire 42 is guided by the second tapered portion 36.

In addition, in the present embodiment, as shown in FIG. 2, the stepped portion 30 coming into contact with the proximal portion 32 of the shaft 12 may be provided in the hub 14, and the material constituting the shaft 12 may cover the stepped portion 30 and be provided further on the proximal side than the stepped portion 30. According to this configuration, when inserting the guide wire 42 from a distal end of the catheter 10 and passing a proximal end of the guide wire 42 through the hub lumen 24, the proximal end of the guide wire 42 can be favorably guided by the material (resin material) of the shaft 12 covering the stepped portion 30 of the hub 14. Accordingly, the proximal end of the guide wire 42 can be smoothly moved in the proximal direction in the hub 14.

Figure 4:
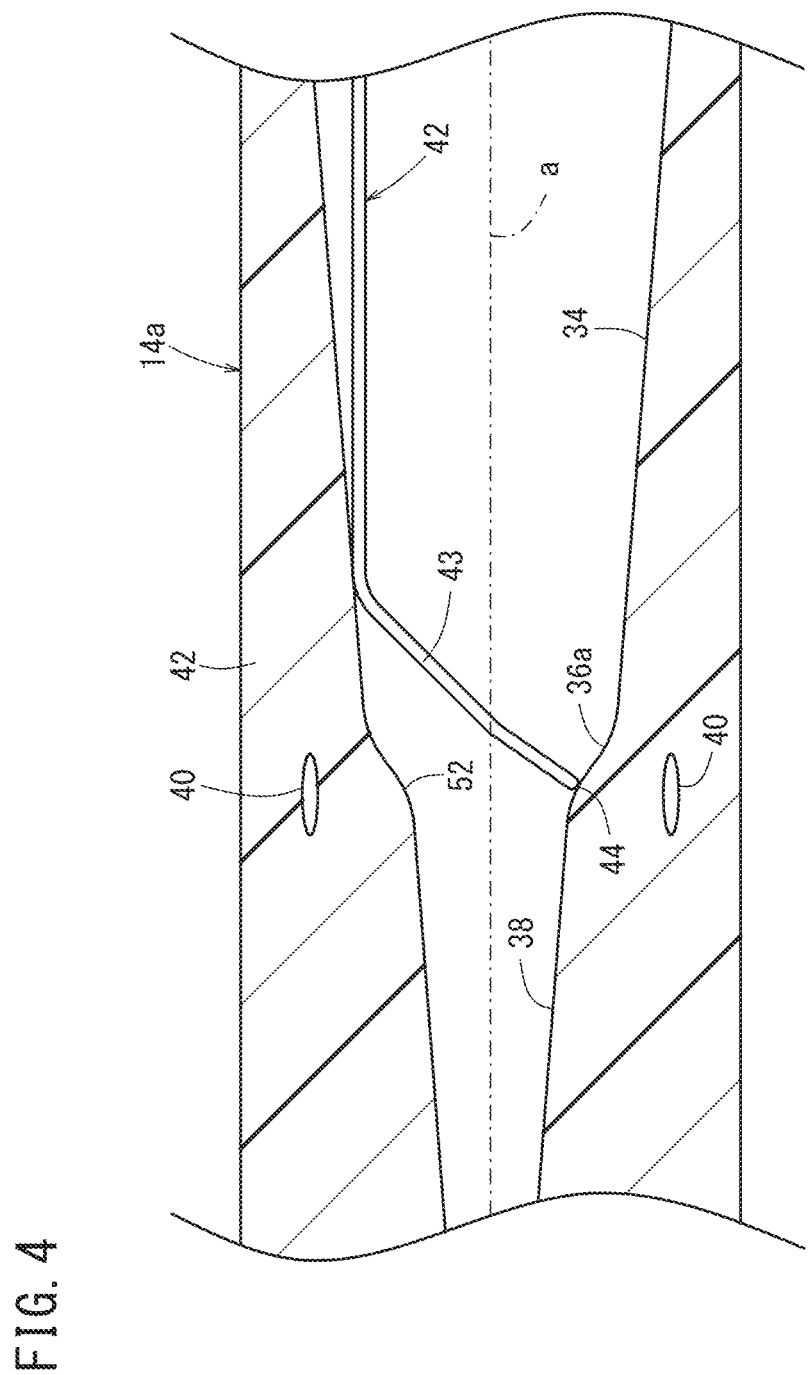
FIG. 4 is a partially omitted longitudinal cross-sectional view of a hub according to a modification example.

In the above-described embodiment as shown, for example, in FIG. 2, the inner shape of the second tapered portion 36 on a longitudinal cross section of the hub is formed in a linear shape. In accordance with an exemplary embodiment, a second tapered portion 36a can be formed in a curved shape, which may be employed like a hub 14a according to a modification example as shown in FIG. 4. For example, the inner shape of the second tapered portion 36a on a longitudinal cross section of the hub 14a can have a portion 52 which is curved so as to be raised toward the inside of the hub 14a. According to this configuration, the frictional resistance between the most distal portion 44 of the guide wire 42 and the inner peripheral surface of the second tapered portion 36a can be reduced by reducing the contact area between the most distal portion 44 of the guide wire 42 and the inner peripheral surface of the second tapered portion 36a due to the contact therebetween nearly becoming a point contact. For this reason, the distal portion 43 of the guide wire 42 can easily pass through the second tapered portion 36a when the distal portion 43 of the guide wire 42 is moved in the distal direction in the hub 14a.

Figure 5:
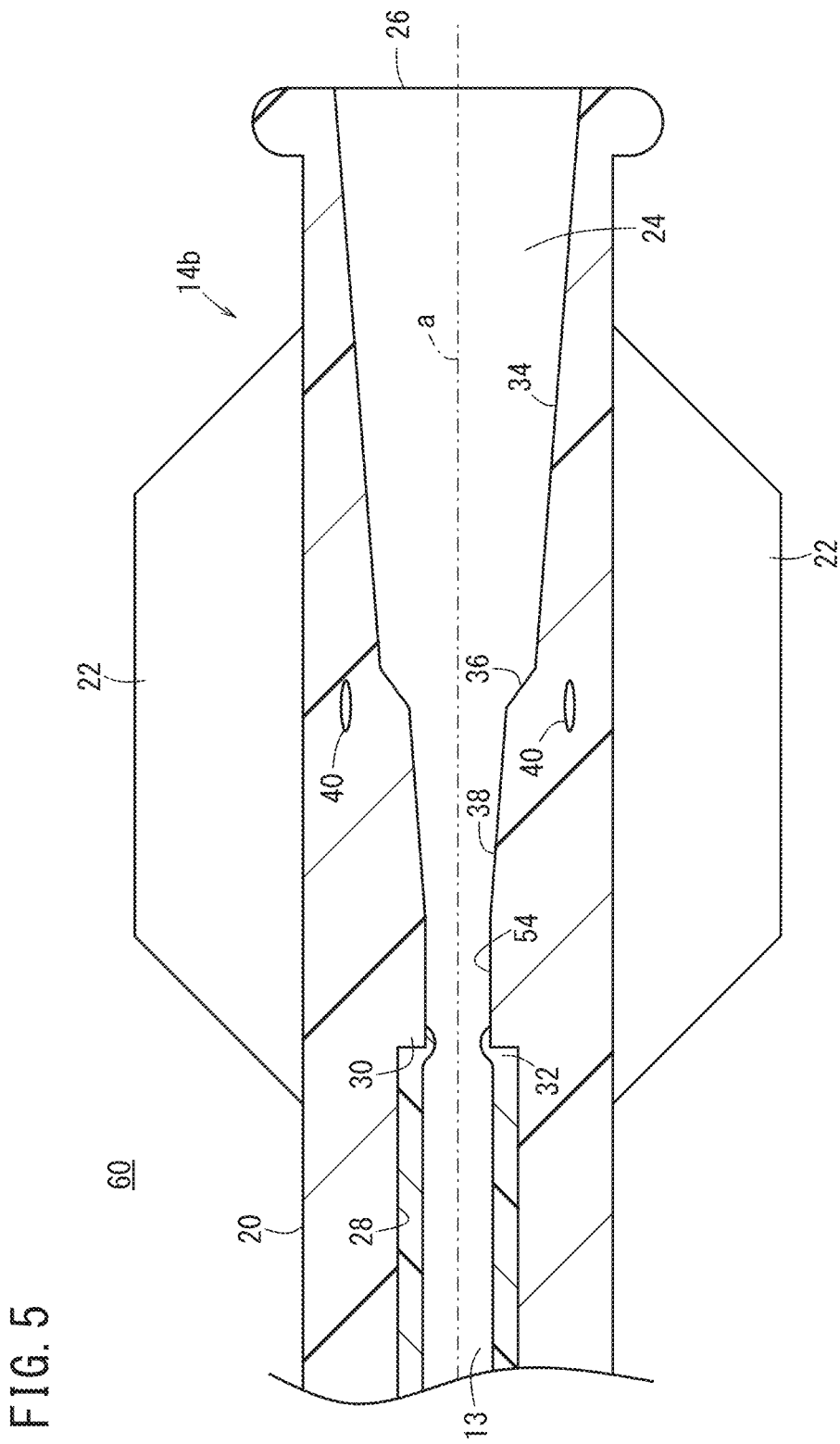
FIG. 5 is a partially omitted longitudinal cross-sectional view of a hub of a catheter according to a modification example.

In the above-described embodiment, the stepped portion 30 is provided at a position of the most distal end of the third tapered portion 38 and a straight portion is not provided between the third tapered portion 38 and the stepped portion 30. However, a hub 14*b* may have a straight portion 54 in which the inner diameter is constant from a distal end of the third tapered portion 38 toward the distal direction like a catheter 60 according to a modification example shown in FIG. 5. According to such a configuration, the same effect as that of the above-described catheter 10 can be obtained.

The detailed description above describes catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
   a shaft constituting a catheter main body; and
   a hub which is provided at a proximal end of the shaft and has a hub lumen that communicates with a lumen of the shaft, and a proximal opening portion, wherein
   the hub has a first tapered portion in which an inner diameter is reduced toward a distal direction from the proximal opening portion, a second tapered portion in which the inner diameter is reduced at a ratio greater than that of the first tapered portion from a distal end of the first tapered portion toward the distal direction, and a third tapered portion in which the inner diameter is reduced at a ratio smaller than that of the second tapered portion from a distal end of the second tapered portion toward the distal direction, and wherein the inner diameter of the first tapered portion, the inner diameter of the second tapered portion, and the inner diameter of the third tapered portion extend continuously from a proximal end of the first tapered portion of the hub to a distal end of the third tapered portion of the hub, and wherein the distal end of the first tapered portion is adjacent to a proximal end of the second tapered portion, and the distal end of the second tapered portion is adjacent to a proximal end of the third tapered portion, and an inner shape of the second tapered portion on a longitudinal cross section of the hub has a portion which is curved so as to be raised toward the inside of the hub.

2. The catheter according to claim 1, wherein
   the hub has a straight portion in which the inner diameter is constant from the distal end of the third tapered portion toward the distal direction.

3. The catheter according to claim 1, wherein
   the hub is formed of a material having transparency, and a plurality of channels extending in an axial direction is provided in a portion of the hub corresponding to the second tapered portion.

4. The catheter according to claim 1, wherein
   a smoothness on an inner peripheral surface varies among the first tapered portion, the second tapered portion, and the third tapered portion.

5. The catheter according to claim 4, wherein the smoothness of the inner peripheral surface of the second tapered portion is greater than the smoothness of the inner peripheral surface of the first tapered portion and the third tapered portion.

6. The catheter according to claim 1, wherein
   a stepped portion coming into contact with a proximal portion of the shaft is provided in the hub, and
   a material constituting the shaft covers the stepped portion and is provided further on a proximal side than the stepped portion.

7. A catheter comprising:
   a shaft; and
   a hub at a proximal end of the shaft, the hub having a hub lumen that communicates with a lumen of the shaft and a proximal opening portion, and wherein
   the hub has a first tapered portion in which an inner diameter is reduced toward a distal direction from the proximal opening portion, a second tapered portion in which the inner diameter is reduced at a ratio greater than that of the first tapered portion from a distal end of the first tapered portion toward the distal direction, and a third tapered portion in which the inner diameter is reduced at a ratio smaller than that of the second tapered portion from a distal end of the second tapered portion toward the distal direction, and wherein the inner diameter of the first tapered portion, the inner diameter of the second tapered portion, and the inner diameter of the third tapered portion extend continuously from a proximal end of the first tapered portion of the hub to a distal end of the third tapered portion of the hub, and wherein the distal end of the first tapered portion is adjacent to a proximal end of the second tapered portion, and the distal end of the second tapered portion is adjacent to a proximal end of the third tapered portion, and an inner shape of the second tapered portion on a longitudinal cross section of the hub has a portion which is curved so as to be raised toward the inside of the hub.

8. The catheter according to claim 7, wherein
   the hub has a straight portion in which the inner diameter is constant from the distal end of the third tapered portion toward the distal direction.

9. The catheter according to claim 7, wherein
   the hub is formed of a material having transparency, and a plurality of channels extending in an axial direction in the second tapered portion.

10. The catheter according to claim 7, wherein
    a smoothness on an inner peripheral surface varies among the first tapered portion, the second tapered portion, and the third tapered portion.

11. The catheter according to claim 10, wherein the smoothness of the inner peripheral surface of the second tapered portion is greater than the smoothness of the inner peripheral surface of the first tapered portion and the third tapered portion.

12. The catheter according to claim 7, wherein
    the hub includes a stepped portion coming into contact with a proximal portion of the shaft.

13. The catheter according to claim 12, wherein
    a material constituting the shaft covers at least the stepped portion.

14. The catheter according to claim 7, wherein the third tapered portion has an angle of inclination, which is constant.

15. A catheter comprising:
    a shaft; and
    a hub at a proximal end of the shaft, the hub having a hub lumen that communicates with a lumen of the shaft and a proximal opening portion, and wherein the hub has a first tapered portion in which an inner diameter is reduced toward a distal direction from the proximal opening portion, a second tapered portion in which the inner diameter is reduced at a ratio greater than that of the first tapered portion from a distal end of the first tapered portion toward the distal direction, and a third tapered portion in which the inner diameter is reduced at a ratio smaller than that of the second tapered portion from a distal end of the second tapered portion toward the distal direction, and a smoothness on an inner peripheral surface varies among the first tapered portion, the second tapered portion, and the third tapered portion, and wherein the smoothness of the inner peripheral surface of the second tapered portion is greater than the smoothness of the inner peripheral surface of the first tapered portion and the third tapered portion, and wherein the inner diameter of the first tapered portion, the inner diameter of the second tapered portion, and the inner diameter of the third tapered portion extend continuously from a proximal end of the first tapered portion of the hub to a distal end of the third tapered portion of the hub, and wherein the distal end of the first tapered portion is adjacent to a proximal end of the second tapered portion, and the distal end of the second tapered portion is adjacent to a proximal end of the third tapered portion, and an inner shape of the second tapered portion on a longitudinal cross section of the hub has a portion which is curved so as to be raised toward the inside of the hub.

16. The catheter according to claim 15, wherein the hub has a straight portion in which the inner diameter is constant from a distal end of the third tapered portion toward the distal direction.

17. The catheter according to claim 15, wherein
the hub is formed of a material having transparency, and
a plurality of channels extending in an axial direction in the second tapered portion.

18. The catheter according to claim 15, wherein
the hub includes a stepped portion coming into contact with a proximal portion of the shaft; and
a material constituting the shaft covers at least the stepped portion.

19. The catheter according to claim 1, wherein the third tapered portion has an angle of inclination, which is constant.

20. The catheter according to claim 15, wherein the third tapered portion has an angle of inclination, which is constant.

\* \* \* \* \*